United States Patent [19]

Graybiel

[11] 4,070,463
[45] Jan. 24, 1978

[54] ANTIMOTION SICKNESS REMEDY

[75] Inventor: Ashton Graybiel, Warrington, Fla.

[73] Assignee: The United States of America as represented by the Secretary of the Navy, Washington, D.C.

[21] Appl. No.: 663,407

[22] Filed: Mar. 3, 1976

[51] Int. Cl.$^2$ .................. A61K 31/54; A61K 31/135
[52] U.S. Cl. .................................... 424/247; 424/330
[58] Field of Search ............................... 424/247, 330

[56] References Cited

PUBLICATIONS

Graybiel et al, NAMRL–1152, 1971.

Primary Examiner—Allen J. Robinson
Attorney, Agent, or Firm—R. S. Sciascia; Philip Schneider; Thomas McDonnell

[57] ABSTRACT

A pharmaceutical composition for the prevention of motion sickness which comprises two parts of promethazine hydrochloride and one part of l-ephedrine sulfate.

2 Claims, No Drawings

ANTIMOTION SICKNESS REMEDY

BACKGROUND OF THE INVENTION

This invention relates generally to biologically effective compounds that aid in the maintenance of bodily homeostasis under stressful situations.

From space travel to the increased everyday air and sea travel there is need for an effective but safe means for minimizing unwanted stressor effects which disturb homeostatic processes in the body. One stressor is usually referred to as motion sickness. The cardinal symptoms of this malaise are increases in salivation, pallor, sweating, drowsiness, and the nausea syndrome, i.e., stomach awareness, stomach discomfort, nausea and vomiting.

The most generally effective remedy, with one exception, is a combination of d-amphetamine sulfate and l-scopolamine. The one exception is an equi-part combination of promethazine hydrochloride and l-ephedrine sulfate. Numerous tests have shown this combination to be extremely effective, if not the most effective anti-motion sickness preventive. While these two homergic drugs individually are not highly effective their combination provides a suprasummation effect. However, equi-part combination of promethazine hydrochloride and l-ephedrine sulphate has shown some objectional side effects, particularly drowsiness.

SUMMARY OF THE INVENTION

It is therefore, an object of this invention to provide a new motion sickness preventative.

Another object of this invention is to provide a single oral fixed-dose of promethazine hydrochloride and l-ephedrine sulfate which is smaller but more effective than the present equi-part dose.

These and other objects are achieved by a single oral fixed-dose of 2 parts of promethazine hydrochloride and 1 part of l-ephedrine sulfate.

DETAILED DESCRIPTION OF THE INVENTION

In the usual practice of this invention, a single oral fixed-dose comprising two parts promethazine hydrochloride and one part l-ephedrine sulfate is taken at least one hour before travel is undertaken and at six hours intervals as long as the need exists. The dose may be in any form, e.g., powder, pill, or capsule and may be taken with or without a liquid or a solid. The recommended dosage is 25 mg of promethazine hydrochloride and 12.5 mg of l-ephedrine sulfate. As with any drug, there are exceptional instances when a larger overall dosage would be necessary, e.g., treatment of a 300 pound person.

The comparative effectiveness of the remedy of this invention was measured by the use of a slow rotation room (SRR). This apparatus resembles a fully enclosed carousel with complete facilities, laboratory, equipment, and communication systems. In a SRR a person is not subjected to stressful stimuli unless he rotates his head out of the room's rotation. Stressful types of accelerative stimuli were generated for the tests by the active rotation of the subjects head and body out of the plane of the room's rotation, which was always counterclockwise. Forty head movements were executed at 1 rpm and were repeated at 1 rpm increments in angular velocity until either the ceiling on the test (30 rpm) or the motion sickness end point was reached. Further details about this apparatus can be found in Graybiel, Ashton, *Contributions of the Space Program to Our knowledge of Motion Sickness.* Astronautica Acta 17: 5-25, 1972 and in Graybiel, Ashton et al, Human Assay of Antimotion Sickness Drugs. Aviation, Space Environmental Med 46: 1107-1118, 1975. In the latter study, an observer, in collaboration with the subject, estimated the levels of severity of the symptoms after every set of forty head movements at a particular rpm. The levels of of motion sickness were given numerical scores according to the diagnostic criteria in Table I. The motion sickness end point for these studies was slight nausea or 12 points, which came first. This endpoint was used in the present comparative test.

TABLE I

| | Diagnostic Categorization Of Different Levels Of Severity Of Acute Motion Sickness | | | | |
|---|---|---|---|---|---|
| Category | Pathognomonic 16 points | Major 8 points | Minor 4 points | Minimal 2 points | AQS* 1 point |
| Nausea syndrome | Nausea III,+ retching or vomiting | Nausea II | Nausea I Epigastric discomfort | Epigastric awareness | |
| Skin | | Pallor III | Pallor II | Pallor I | Flushing/Subjective warmth ≧II |
| Cold sweating | | III | II | I | |
| Increased salivation | | III | II | I | |
| Drowsiness | | III | II | I | |
| Pain | | | | | Headache (persistent)≧II |
| Central nervous system | | | | | Dizziness (persistent) Eyes closed≧II Eyes open III |

| | | Levels of Severity Identified by Total Points Scored | | |
|---|---|---|---|---|
| Frank Sickness (FS) ≧16 points | Severe Malaise (M III) 8 – 15 points | Moderate Malaise A (M IIA) 5 – 7 points | Moderate Malaise B (M IIB) 3 – 4 points | Slight Malaise (M I) 1 – 2 points |

*AQS - Additional qualifying symptoms
+III - severe or marked, II - moderate, I - slight A difficult aspect of measuring the effect of the drugs in any comparison study is accounting for variations in placebo responses. In the present comparative test three criteria were used to establish a placebo baseline. When the variations were similar and small, i.e., 2 rpm, a means value baseline was used. When there was a rise or fall in the scores in the placebo range but the variation was between 2 and 3 rpm, the placebo level was indicated by one or more best-fit sloped baselines. When the range in placebo scores was greater than 3 rpm, the placebo level was estimated relying heavily on the immediately preceding placebo score.

The efficacy of the drugs in the present comparison tests on motion sickness susceptibility was described as beneficial, inconsequential or determental, depending on the motion sickness end point (rpm of the device) when a drug was administered compared with the placebo level. The range for "inconsequential" motion sickness response was defined as lying within limits representing twice the values of the placebo range i.e., the range between the extremes in placebo response. To qualify as a "beneficial" effect the difference between the placebo baseline score and the motion sickness end point score had to equal or exceed twice the difference (in rpm) between the placebo and the score indicating the upper limit of the inconsequential range. When the motion sickness end point score equaled or exceeded twice the difference between the placebo baseline and the lower limit of the inconsequential range the therapeutic effect was termed "detrimental".

The subjects in the following comparison test were all male paid volunteers between the ages of 21 and 28. They were selected on the basis of a comprehensive medical evaluation and the absence of vestibular defects determined by specific tests on canalicular, otolithic, and combined vestibular functions.

The results are given in Table II for the aforementioned comparative test of a number of combinations and dosages of promethazine hydrochloride (P) and l-ephedrine sulfate (E). The number following the letters designating promethazine hydrochloride or l-ephedrine sulfate designate the amounts thereof in milligrams.

ability is low in the case of Sample No. 5. If the two are administered together in equal amounts, (Sample No. 3), a significant benefit is obtained. Sample No. 1 shows that doubling the amount of l-ephedrine sulfate does not improve the efficacy of the combination even though more of the drug is consumed. If promethazine hydrochloride is halved (Sample No. 2), the effectiveness of the combination is practically eliminated. On the other hand, if the l-ephedrine sulfate is halved (Sample No. 4), the effectiveness is substantially the same as the equi-part combination in terms of beneficial response, but is considerably more effective in terms of the strength of tolerated stimuli.

In summary the 2:1 combination of the present invention marks an important improvement in treating motion sickness in terms of stimulus tolerance and in terms of reduced side effects. The side effects are sufficiently diminished to permit the remedy to be administered to a person for a period of several days.

Obviously many modifications and variations of the present invention are possible in light of the above teachings. It is therefore to be understood that, within the scope of the appended claims, the invention may be practiced otherwise than as specifically described.

What is claimed and desired to be secured by Letters Patent of the United States is:

1. A pharmaceutical composition for the prevention of motion sickness which comprises two parts of promethazine hydrochloride and one part of l-ephedrine sulfate.

2. The composition of claim 1 wherein the amount of promethazine hydrochloride is 25 mg.

TABLE II

| Sample No. | Sample NO. | Drug Drug | MEAM RPM of End point w/drug | MEAN RPM of End point w/placebo | RPM Improvement | % RPM Improvement | % Response beneficial |
|---|---|---|---|---|---|---|---|
| 1 | 18 | P25E50 | 16.4 | 11.6 | 4.8 | 38.0 | 83.3 |
| 2 | 7 | P12.5E25 | 14.0 | 12.3 | 1.7 | 13.5 | 28.6 |
| 3 | 11 | P25E25 | 15.0 | 10.0 | 5.0 | 50.0 | 90.9 |
| 4 | 7 | P25E12.5 | 17.9 | 9.5 | 8.4 | 89 | 85 |
| 5 | 8 | P25 | 16.9 | 13.7 | 3.2 | 14.6 | 50.0 |
| 6 | 8 | E50 | 15.6 | 13.6 | 2.0 | 14.0 | 50.0 |
| 7 | 10 | E25 | 12.1 | 11.2 | 0.9 | 8.0 | 10.0 |

If either of the constituents is administered alone, efficacy is poor in the case of Sample No. 7 and accept-

* * * * *